(12) United States Patent
Hauge

(10) Patent No.: US 7,975,689 B2
(45) Date of Patent: Jul. 12, 2011

(54) APPARATUS FOR MAINTAINING A SURGICAL AIRWAY AND METHOD OF THE SAME

(76) Inventor: Russ Hauge, Woodbury, MN (US)

( * ) Notice: Subject to any disclaimer, the term of this patent is extended or adjusted under 35 U.S.C. 154(b) by 975 days.

(21) Appl. No.: 11/445,797

(22) Filed: Jun. 2, 2006

(65) Prior Publication Data

US 2006/0272647 A1 Dec. 7, 2006

Related U.S. Application Data

(60) Provisional application No. 60/687,405, filed on Jun. 3, 2005.

(51) Int. Cl.
*A61M 16/00* (2006.01)
(52) U.S. Cl. .......... 128/200.26; 128/207.14; 128/207.15
(58) Field of Classification Search ............. 128/200.26, 128/201.26, 206.29, 207.11, 207.14, 207.15, 128/207.17, 207.29
See application file for complete search history.

(56) References Cited

U.S. PATENT DOCUMENTS

| | | | | |
|---|---|---|---|---|
| 2,127,215 | A | * | 8/1938 | Gwathmey ............... 128/207.14 |
| 2,820,457 | A | * | 1/1958 | Phillips .................... 128/200.26 |
| 3,908,665 | A | * | 9/1975 | Moses ...................... 128/207.14 |
| 5,474,063 | A | | 12/1995 | Riendeau |
| 5,653,229 | A | * | 8/1997 | Greenberg ............... 128/207.15 |
| 5,937,858 | A | * | 8/1999 | Connell .................... 128/207.14 |
| 5,950,624 | A | | 9/1999 | Hart |
| 6,256,524 | B1 | * | 7/2001 | Walker et al. .................. 600/340 |
| 2003/0000534 | A1 | * | 1/2003 | Alfery ...................... 128/207.14 |
| 2003/0034036 | A1 | | 2/2003 | Waldeck |
| 2004/0129272 | A1 | * | 7/2004 | Ganesh et al. ........... 128/207.14 |
| 2004/0221851 | A1 | | 11/2004 | Madsen |

FOREIGN PATENT DOCUMENTS

| | | |
|---|---|---|
| DE | 197 34 821 | 2/1999 |
| EP | 1 003 584 | 5/2000 |
| WO | 02/055143 | 7/2002 |

* cited by examiner

*Primary Examiner* — Quang D Thanh
(74) *Attorney, Agent, or Firm* — Hamre, Schumann, Mueller & Larson, P.C.

(57) ABSTRACT

An apparatus for maintaining a surgical airway and method for the same includes an elongated body insertable orally into a patient. The elongated body defines leading and trailing ends. An opening is defined through the leading and trailing ends, such that surgical equipment may be insertable through the opening of the elongated body. A securing member is connected to the trailing end. The securing member holds the elongated body in a position such that an airway remains open to treat the patient, while supporting oxygen flow to the patient.

3 Claims, 3 Drawing Sheets

APPARATUS FOR MAINTAINING A SURGICAL AIRWAY AND METHOD OF THE SAME

CROSS-REFERENCE AND PRIORITY DATA

This application claims the benefit of priority of U.S. Provisional Application No. 60/687,405, filed on Jun. 3, 2005, and entitled APPARATUS FOR MAINTAINING A SURGICAL AIRWAY AND METHOD OF THE SAME and which is incorporated herewith by reference in its entirety.

FIELD

The invention relates to an apparatus for maintaining a surgical airway and method of the same. More particularly, an apparatus is disclosed that is inserted into and held within a patient's mouth.

BACKGROUND

Devices for maintaining a surgical airway are well known and widely used, such as by enabling a patient to continue breathing during surgical and outpatient procedures. Typically, such devices may be employed in gastro and/or bronchial surgical procedures, and may be employed in outpatient applications, for instance, where patients experience sleep apnea.

In previous applications, a nasal cannula and bite block combination have been used. However, difficulties arise where a patient does not have a nasal airway or cannot breathe through his/her nose. Employing a nasal cannula and bite block limits the flow of oxygen to a patient. Such devices only deliver 28%-40% oxygen concentration to the patient. Furthermore, the bite block may not be optimally secured, and thus may not always stay in place. Such devices also require extensive modification to be capable of monitoring carbon dioxide.

While these previous applications have provided some advancement for maintaining a surgical airway, improvements may yet be made to such devices. There is a need for an apparatus for maintaining a surgical airway that provides optimal oxygen flow, and that has the capability to monitor and detect end carbon dioxide ($ETCO_2$). A device is desirable that can be better secured so as to stay in place, while sufficiently maintaining access to the airway. Improvements may still be made to an apparatus for maintaining a surgical airway that requires less equipment and that can be conveniently used.

SUMMARY

It is the purpose in the descriptions hereafter to overcome these difficulties, thereby providing an improved apparatus for maintaining a surgical airway and method for the same.

In one embodiment, an apparatus for maintaining a surgical airway includes an elongated body insertable orally into a patient. The elongated body defines leading and trailing ends. An opening is defined through the leading and trailing ends, such that surgical equipment may be insertable into the elongated body and through the opening. A securing member is connected to the trailing end. The securing member holds the elongated body in a position such that an airway remains open to treat the patient while supporting oxygen flow to the patient.

In one preferred embodiment, an apparatus for maintaining a surgical airway includes an adapter connected to the trailing end of the elongated body. The adapter is at least partially disposed external to a mouth of the patient. The adapter defines an access to the opening.

In one preferred embodiment, an adapter includes at least one securing member support. The securing member support engages the securing member to hold the elongated body and adapter in a position such that an airway of the patient remains open.

In one preferred embodiment, an adapter defines at least one aperture therethrough. The aperture(s) enabling support of flow conduits. Preferably, the flow conduits are capable of delivering fluids to the patient and monitoring fluid release from the patient, for example delivering supplemented oxygen or monitoring end tidyl carbon dioxide.

In yet another embodiment, the elongated body defines an arching portion proximate the leading end. The arching portion enables the elongated body to maintain the tongue of the patient in a posterior position, so as to prevent a gag reflex when the elongated body is inserted.

Preferably, the apparatus is constructed and arranged for one-time use.

The apparatus for maintaining a surgical airway provides an improved surgical airway. The apparatus provides a more secure surgical airway that may be disposed after one-time use. The elongated body provides a structure that includes bite block protection and keeps the tongue from obstructing the airway (oral pharynx). The apparatus is capable for monitoring end tidyl carbon dioxide release of a patient, so that oxygen may be delivered sooner to the patient. The apparatus also provides supplemental oxygen flow to the patient at a higher concentration and at improved rates without impeding access to the airway.

The apparatus may be employed in various applications requiring maintenance of a surgical airway. Such applications include esophago-gastro dilatations (EGDs), gastroscopies, bronchoscopies, and deep monitored anesthesia care (MAC) cases. The apparatus further aids in other outpatient procedures, such as those patients suffering from sleep apnea. The apparatus for maintaining a surgical airway requires less equipment for use, for example, no mask is required to cover a patient's face. The apparatus provides an elegant design with improved performance and user convenience.

These and other various advantages and features of novelty, which characterize the apparatus for maintaining a surgical airway, are pointed out in the following detailed description. For better understanding of the apparatus, its advantages, and the objects obtained by its use, reference should also be made to the drawings which form a further part hereof, and to the accompanying descriptive matter, in which there are illustrated and described specific examples of the apparatus.

BRIEF DESCRIPTION OF THE DRAWINGS

Like reference numbers generally indicate corresponding elements in the Figures. The embodiments illustrated are exemplary only and are in accordance with the principles of the present invention.

DETAILED DESCRIPTION OF THE PREFERRED EMBODIMENT

Figures 1, 1A:
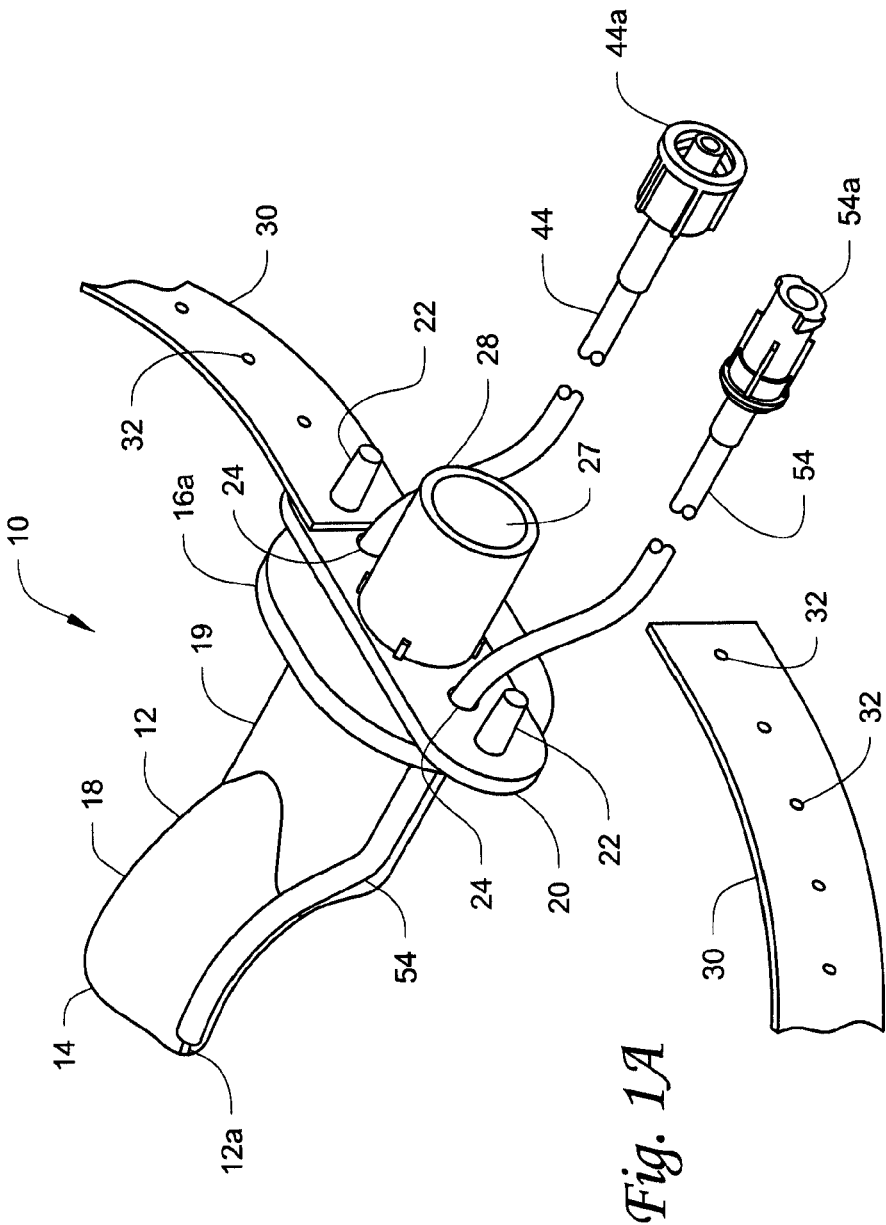
FIG. 1 represents an elevated perspective view of one embodiment of an apparatus for maintaining a surgical airway.
FIG. 1A represents a portion of one embodiment of a securing member which is shown in FIG. 1.
Figure 2:
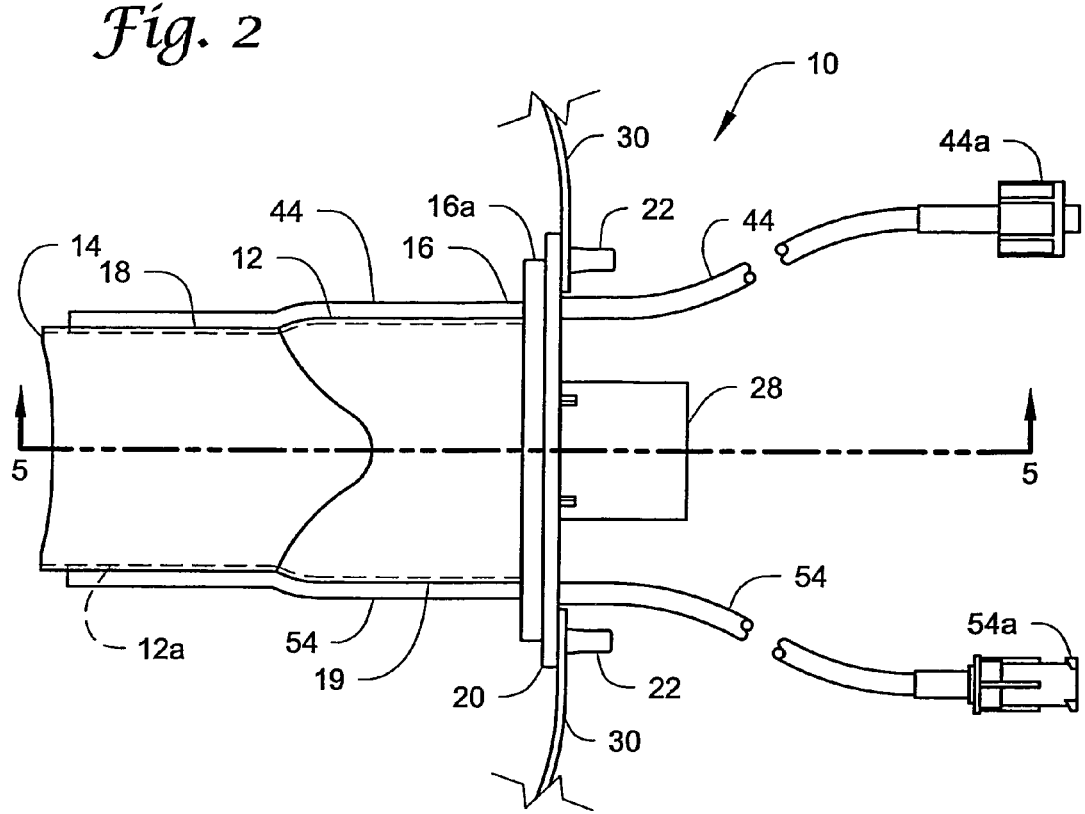
FIG. 2 represents an elevated top view of the apparatus of FIG. 1.
Figure 3:
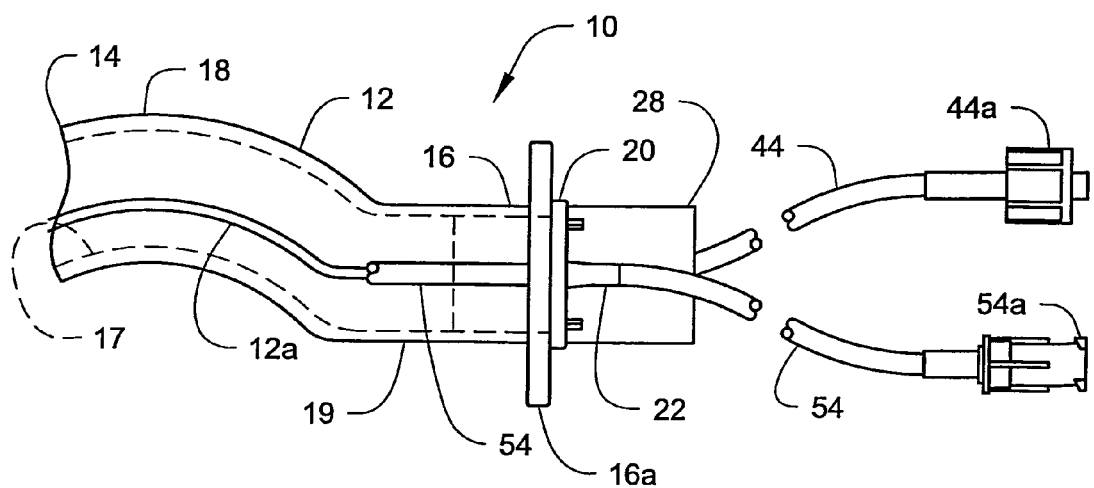
FIG. 3 represents an elevated side view of the apparatus of FIG. 1.
Figure 4:
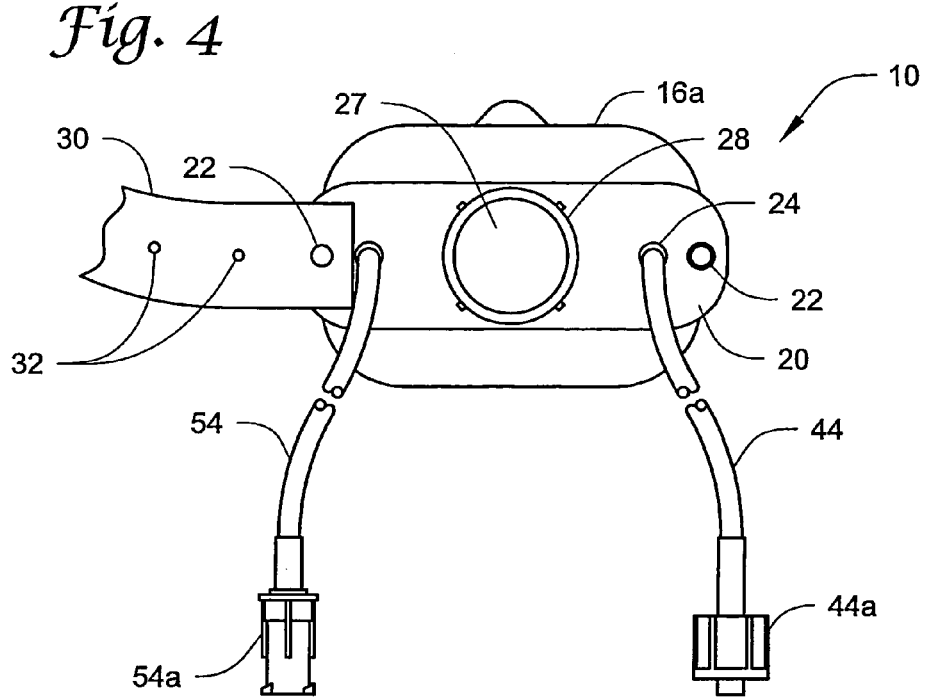
FIG. 4 represents an end view of the apparatus of FIG. 1 showing one embodiment of a leading end.
Figure 5:
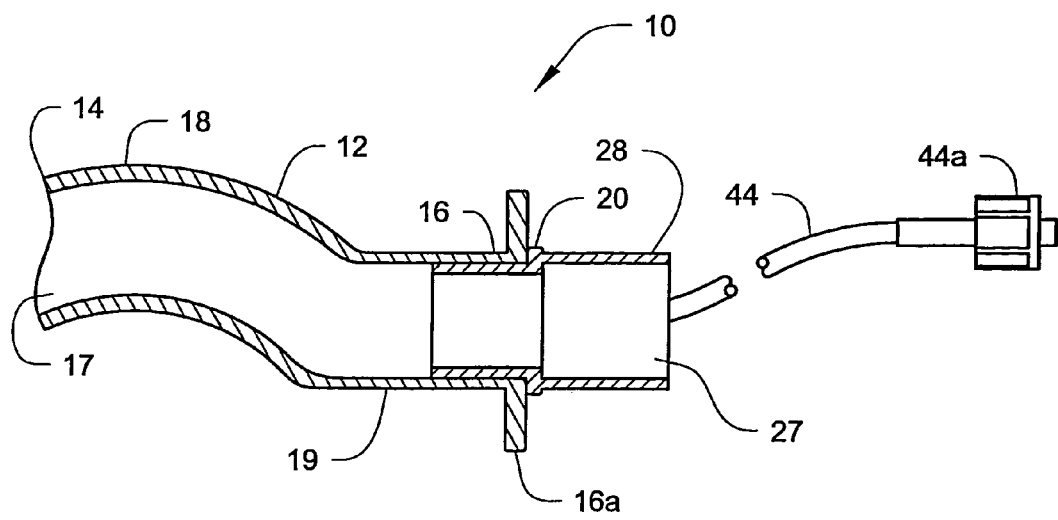
FIG. 5 represents a side sectional view of the apparatus of FIG. 1.

One exemplary embodiment of an apparatus for maintaining a surgical airway 10 is provided in FIGS. 1-5.

The apparatus for maintaining a surgical airway 10 (hereafter the apparatus) includes an elongated body 12 defining first and second ends. The elongated body 12 is insertable orally into a mouth of a patient. One of the first or second ends of the elongated body 12 defines a leading end 14. The other of the first or second ends defines a trailing end 16. The leading end 14 is orally insertable into the patient with the trailing end 16 being orally insertable behind the leading end 14. Disposed proximately to the leading end 14, the elongated body 12 includes a lead portion 18. Disposed proximately to the trailing end 16, the elongated body includes a trail portion 19. The lead portion 18 and trail portion 19 will be further discussed below.

An opening 17 is defined through the leading and trailing ends 14, 16. Preferably, surgical equipment may be insertable into the elongated body 12 through the opening 17. In some preferred applications, such as in gastro and/or bronchoscope procedures or as in suctioning procedures, the opening enables treatment of the patient through the opening 17 with the required medical instruments. The opening 17 provides an airway to be maintained open when the elongated body 12 is inserted orally into the patient. The opening 17 thus enables insertion of treatment instruments, and supports airflow and oxygen flow to the patient for him/her to breathe.

Preferably, a securing member 30 is connected to the trailing end 16. The securing member 30 holds the elongated body 12 in position during use, and prevents dislodgment of the same. As one exemplary embodiment, the securing member 30 may be a resilient strap with elastic physical characteristics. The securing member 30 may include a plurality of securing holes 32 therethrough and along a side surface of the strap (see also FIG. 1A). The securing holes 32 removably attach with a support on the elongated body 12 or suitable adapter (described below) that may be used in connection with the elongated body 12. Preferably, opposing ends of the securing member 30 are removably attached proximate the trailing end 16 of the elongated body 12 by the securing holes 32.

When the elongated body 12 is inserted orally into a patient, the securing member 30, attached to the elongated body 30 may be dressed around a patient's neck or lower head to secure the apparatus 10. The plurality of securing holes 32 enables fine adjustment of the securing member 30, so as to provide an optimal and comfortable fit for the patient. The securing member 30 thus stabilizes the elongated body 12, such that the opening 17 can maintain an open airway of the patient for treatment, while supporting oxygen flow to the patient.

The elongated body 12 may be constructed of any number of materials, including but not limited to molded softer plastics. It will be appreciated that such materials are exemplary only, as other materials may be equally or more suitable. It will be further appreciated that the elongated body 12 may be limited only to the extent in providing a suitably rigid elongated body structure that does not collapse or cannot be bitten down on while maintaining an open airway of the patient.

The securing member 30 may be constructed of any number of materials, including but not limited to a soft elastic rubber. It will be appreciated that such materials are exemplary only, as other materials may be equally suitable. The material employed for constructing the securing member 30 may only be limited by such physical characteristics necessary for securing the elongated body 12 as described, and for providing a comfortable fit around a patient's neck or lower head.

In another preferred embodiment for the apparatus for maintaining a surgical airway 10, an adapter 20 is connected to the trailing end 16 of the elongated body 12. Preferably, the adapter 20 is inserted into the elongated body 12 at the trailing end 16, and is at least partially disposed external to a mouth of the patient. The adapter 20 includes an access 27 to the opening 17, such that surgical equipment may be inserted into the access 27 to reach the opening 17 of the elongated body 12. Preferably, the access 27 may be defined by an extended portion 28. The extended portion 28 provides a structure that extends outward from the mouth of a patient, so that the access 27 may enable insertion of surgical equipment into the opening 17.

As one example only, the extended portion 28 is illustrated as a hollow cylindrical structure defining the access 27. It will be appreciated, however, that such a configuration is exemplary only, as other configurations and shapes may be equally or more suitable. As one non-limiting example, the extended portion may be an oval-like or other arcuate shape.

In another preferred embodiment, the adapter 20 includes at least one securing member support 22. As shown, two securing member supports 22 are illustrated on opposite sides of the access 27. It will be appreciated that additional supports may be employed as desired or necessary for supporting the securing member on the adapter 20, and may be disposed in other locations on the adapter 20 than that illustrated. The securing member supports 22 engage the securing member 30 to hold the elongated body 12 and adapter 20 in a position such that an airway of the patient remains open. Preferably, the securing member supports 22 are protrusions or prongs extending outward from the trailing end 16 in the same direction as the extended portion 28. The prongs 22 attach the securing member 30 through the securing holes 32 to connect the adapter 20 to the securing member 30.

It will be appreciated, however, that the prong and hole structure is merely exemplary as other securing methods may be employed that are equally or more suitable. It will be further appreciated that in any event where an adapter is not employed, the securing member 30 may also be attached to the elongated body 12 directly. Such as, for instance, in a configuration where there is no separate adapter piece, and where the elongated body 12 includes an extended portion and access integrally formed thereon, and the elongated body 12 includes securing member supports integrally formed thereon.

In another embodiment, the adapter 20 defines at least one aperture therethrough. As shown, the adapter 20 includes two apertures 24 oppositely disposed of the access 27. The apertures 24 enable support of first and second flow conduits 44, 54. Preferably, the flow conduits 44, 54 are capable of delivering a supplemented supply of oxygen, and are capable of monitoring end tidyl carbon dioxide along side surfaces of the elongated body 12.

As one example, the first flow conduit 44 may be a tubing insertable through one of the apertures 24. Preferably, the flow conduit 44 is constructed of a reinforced material so that, in the event of bite down by the patient, the flow conduit 44 will not collapse or be obstructed. It will be appreciated that the flow conduit 44 is a reinforced material and may be similar to the plastic material of the elongated body 12. It will be further appreciated that the flow conduit 44 is to be suitably rigid for patient use and for preventing such undesired effects. The flow conduit 44 may be disposed along a side groove 12a of the elongated body 12. The side groove 12a supports the flow conduit along a side surface of the elongated body 12. An inserted end of the first conduit 44 may enable carbon dioxide to be released therein, so that $ETCO_2$ may be monitored. The opposite end may include a first fitment 44a that connects with a carbon dioxide detector (not shown) to monitor $ETCO_2$.

With such capability, the apparatus 10 may monitor a patient's oxygenation more effectively, so that oxygen can be delivered sooner to a patient in need. When the $ETCO_2$ increases for example, then the oxygen level decreases. In previous applications, oxygen levels had been monitored by pulse oximetry. Such methods, however, have required waiting on a perfusion time of 15-30 seconds. In the embodiment provided by the apparatus 10, oxygen levels can be determined at a sooner time, so that oxygen may be delivered to a patient before a critical point of need.

As another example, the second flow conduit 54 may be a tubing insertable through the other one of the apertures 24. Preferably, the flow conduit 54 is constructed of a reinforced material so that, in the event of bite down by the patient, the flow conduit 54 will not collapse or be obstructed. It will be appreciated that the flow conduit 54 is a reinforced material and may be similar to the plastic material of the elongated body. It will be further appreciated that the flow conduit 54 is to be suitably rigid for patient use and for preventing such undesired effects. The flow conduit 54 may be along another side groove 12a of the elongated body 12. The side groove 12a supports the flow conduit along a side surface of the elongated body 12. An inserted end of the second conduit 54 may exit a supplement supply of oxygen to the patient. The opposite end may include a second fitment 54a that connects with an oxygen supply source (not shown).

Although two flow conduits are shown, it will be appreciated that more or less than two conduits may be employed as necessary or desired for delivery of other fluids or for other monitoring purposes. It will be appreciated that supplying oxygen and monitoring end tidyl carbon dioxide are preferred examples only of fluids that the apparatus supports. It may be desirable to deliver or monitor other fluids including other gases and liquids. The term "fluid" is construed broadly to include any medium that can be made to flow.

The adapter 20 may be constructed from any number of materials, including but not limited to molded soft plastics. The adapter may be constructed of any material that is suitably rigid and similar to the elongated body 12 for maintaining an open airway of the patient. It will be appreciated that such materials are exemplary only, as other materials may be equally or more suitable. It will further be appreciated that the adapter 20 may be integrally formed with the elongated body 12, whereby the elongated body 12 and adapter 20 may be represented as a one piece unit.

In yet another embodiment, the elongated body 12 includes a lead portion 18 proximate the leading end 12. Preferably, the lead portion 18 defines an arching portion. The arching portion defines an overcurve and an undercurve. Preferably, the overcurve contacts the upper ridge of a patient's mouth at the hard palate and just before the soft palate. Preferably, the arching undercurve contacts the tongue of the patient. The arching portion enables the elongated body 12 to maintain a tongue of the patient in a posterior position. More preferably, the lead portion is configured of a length such that it does not extend deep enough into the soft palate, and so as to prevent a gag reflex by a patient when the elongated body 12 is inserted.

In another embodiment of the elongated body 12, a flange 16a is disposed at the trailing end 16. Preferably, the flange 16a is annularly disposed about the outer surface of the elongated body 12. The flange 16a may enable a patient to comfortably fit the apparatus 10 around his/her mouth, and help to prevent the entire apparatus 10 from entering the patient.

The elongated body 12 with its rigid outer structure provides a bite block to prevent a patient from closing his/her mouth and prevent the airway from collapsing. Thus, the bite block function facilitates maintaining the airway in an open position. In conditions where a patient may experience a seizure, for example, the outer structure of the elongated 12 prevents the opening from collapsing even when a patient bites down on the apparatus 10. Preferably, the apparatus 10 is constructed and arranged for one-time use, and preferably on a per patient basis.

The apparatus 10 may include a variety of dimensions suitable for both adults and children. As an example for adult sizes, the elongated body 12 may include a length from leading end 14 to trailing end 16 that is approximately 4.0 inches. A width of the elongated body 12 may have a range from approximately 1.0 inches to 1.5 inches and suitable for both males and females. The opening 17 may include a width as high as approximately 1⅛ inches. The flange 16a may have a height of approximately 1.5 inches. A height or thickness of the elongated body 12 may approximately be 0.75 inches. A height of the adapter 20 may approximately have a range of ⅝ inches to ½ inches.

It will be appreciated, however, that such dimensions are exemplary only. Other dimensions may be employed that are equally or more suitable to achieve the desired functions of the apparatus 10. Thus, the dimensions of the apparatus 10, and particularly of the elongated body 12, are only limited to appropriate sizes related to age and gender, and may be modified for optimal results.

The apparatus 10 provides a more secure surgical airway that may be disposed after one-time use. The elongated body 12 provides a structure that includes bite block protection and keeps the tongue from obstructing the airway (oral pharynx). The apparatus is capable for monitoring $ETCO_2$ of a patient. Supplemental oxygen flow may be provided to the patient at a higher concentration and at improved rates, without impeding access to the airway. The apparatus provides that oxygen concentrations may be improved as high as 60-80%. Furthermore, the apparatus for maintaining a surgical airway requires less equipment for its use, for example, no mask is required to cover a patient's face. The apparatus provides an elegant design with improved performance and user convenience.

The apparatus may be employed in known medical procedures, such as but not limited to, gastro and/or bronchial surgical procedures, and may be employed in outpatient applications, for instance, where patients experience sleep apnea. As some additional examples only, such procedures and applications may include use in esophago-gastro dilatations (EGDs), gastroscopies, bronchoscopies, and in deep monitored anesthesia care (MAC) cases. It will be appreciated that the apparatus may be employed in any number of applications and procedures, and is not limited to those listed. It will be appreciated that any procedure requiring an open airway of a patient to be maintained may employ the apparatus as already described.

The above specification provides a complete description of the composition, manufacture and use of an improved apparatus for maintaining a surgical airway in accordance with the principles of the present invention. Since many embodiments an apparatus for maintaining a surgical airway can be made without departing from the spirit and scope of the invention, the invention resides in the claims hereinafter appended.

The invention claimed is:

1. An apparatus for maintaining a surgical airway, comprising:
   an elongated body insertable orally into a patient, the elongated body including a first end and a second end, one of the first or second ends defining a leading end insertable orally into a patient, the other of the first and second ends defining a trailing end, the elongated body has a width approximately 1.0 to 1.5 inches, the elongated body including an opening extending through the leading and trailing ends, the opening enabling insertion of surgical equipment therethrough for use in treatment of the patient, and the opening supporting airflow to the patient,
      the elongated body further comprising an arching portion proximate the leading end, the arching portion comprising an overcurve and an undercurve, the overcurve being adapted to contact the upper ridge of the mouth of the patient at the hard palate and just before the soft palate, and the undercurve being adapted to contact the tongue of the patient,
         the arching portion being constructed of a length so that the overcurve ends just before the soft palate, the arching portion being configured to enable the elongated body to maintain the tongue of the patient in a posterior position and prevent a gag reflex by the patient when the elongated body is inserted,
   a securing member connected to the trailing end, wherein the securing member is configured to hold the elongated body in a position so that an airway of the patient remains open when the elongated body is orally inserted into the patient, the securing member comprises a resilient strap adapted to be supported on the elongated body and dressed around a head or lower neck of the patient, the resilient strap includes a plurality of securing holes, so that the resilient strap is adapted to be removably attached with the elongated body;
   two securing member supports disposed on a portion connected to the elongated body, the securing member supports adapted to engage the securing member so as to hold the elongated body in position when in use, the securing member supports are protrusions extending outward relative to the trailing end;
   an access disposed at the trailing end for accessing the opening of the elongated body, the access including an extended portion that extends outward relative to the trailing end in the same direction as the protrusion and externally of the mouth of the patient; and
   two flow conduits disposed at sides of the elongated body, one of the flow conduits is deliverable of oxygen to the patient, so as to maintain oxygen level to the patient during operating or surgical procedures, the other flow conduit is receivable for carbon dioxide exhaled by the patient, so as to enable monitoring of end tidyl carbon dioxide of the patient,
   wherein one of the two flow conduits is disposed between the access and one of the securing member supports and the other of the two flow conduits is disposed between the access and the other of the securing member supports.

2. The apparatus according to claim 1, wherein the extended portion is integrally formed on the elongated body.

3. The apparatus according to claim 1, wherein the securing member supports are arranged beyond the width of the elongated body when the apparatus is viewed from a top view.

* * * * *